(12) United States Patent
Ito et al.

(10) Patent No.: US 7,651,834 B2
(45) Date of Patent: Jan. 26, 2010

(54) PHOTOSENSITIVE COMPOUND, PHOTOSENSITIVE COMPOSITION, METHOD FOR RESIST PATTERN FORMATION, AND PROCESS FOR DEVICE PRODUCTION

(75) Inventors: Toshiki Ito, Kawasaki (JP); Takako Yamaguchi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 377 days.

(21) Appl. No.: 11/746,747

(22) Filed: May 10, 2007

(65) Prior Publication Data

US 2007/0287105 A1 Dec. 13, 2007

(30) Foreign Application Priority Data

Jun. 9, 2006 (JP) ............................. 2006-161524
Feb. 6, 2007 (JP) ............................. 2007-027368

(51) Int. Cl.
*G03F 7/30* (2006.01)
*G03F 7/004* (2006.01)

(52) U.S. Cl. .................................. 430/326; 430/270.1

(58) Field of Classification Search .............. 430/270.1, 430/326
See application file for complete search history.

(56) References Cited

U.S. PATENT DOCUMENTS

| | | | |
|---|---|---|---|
| 4,859,563 | A | 8/1989 | Miura et al. |
| 5,314,782 | A * | 5/1994 | Lazarus et al. ............... 430/165 |
| 6,358,665 | B1 | 3/2002 | Pawlowski et al. |
| 6,849,391 | B2 | 2/2005 | Yamaguchi et al. |
| 7,022,463 | B2 | 4/2006 | Yamaguchi et al. |
| 2002/0012867 | A1 | 1/2002 | Yasuda |
| 2005/0221222 | A1 | 10/2005 | Ito et al. |
| 2006/0003269 | A1 | 1/2006 | Ito et al. |
| 2006/0014108 | A1 | 1/2006 | Ito et al. |
| 2007/0212806 | A1* | 9/2007 | Ito ............................... 438/99 |

FOREIGN PATENT DOCUMENTS

CN 1274433 A 11/2000

| | | |
|---|---|---|
| EP | 0962825 A1 | 12/1999 |
| EP | 1033624 A1 | 9/2000 |
| JP | 62-69263 A | 3/1987 |
| JP | 62-223156 A | 10/1987 |

OTHER PUBLICATIONS

Taku Hirayama et al., "New Photoresist Based on Amorphous Low Molecular Weight Polyphenols," 17(3) J. Photopolymer Sci. Technol. 435-40 (2004).
Grant A. Krafft et al., "Photoactivable Fluorophores. 3. Synthesis and Photoactivation of Fluorogenic Difunctionalized Fluorescein," 110 J. Am. Chem. Soc. 301-03 (1988).
Alan R. Katritzky, "Model Compounds of Caged Capsaicin: Design, Synthesis, and Photoreactivity," 68 J. Org. Chem. 9100-04 (2003).
Shigeru Kubota et al., "Preparation of Positive Photoreactive Polyimides and Their Characterization," 33 J. Appl. Polym. Sci. 1763-75 (1987).
Nihiskubo Tadatomi et al., "Study of Photopolymers. XXXIV. Esterification and Esterification Reactions of Polymers with (o, m, or p)-Bromomethylnitrobenzene Using the DBU Method and the Photochemical Properties of the Resulting Polymers," 28(1) J. Polym. Sci. Part A 105-17 (1990).
Tokuyuki Honda et al., "What determines the ultimate resolution? The critical relationship between exposure tools and photoresists," Proc. of SPIE, vol. 6154, 615422, pp. 1-9 (2006).

* cited by examiner

*Primary Examiner*—John S Chu
(74) *Attorney, Agent, or Firm*—Fitzpatrick, Cella, Harper & Scinto (57) ABSTRACT

A process for forming a resist pattern comprises the steps of applying on a substrate to form a photosensitive resist layer a photosensitive composition comprising at least one photosensitive compound having, in the molecule, two or more structural units represented by $C_6R_{2-6}$—$CHR_1$—$OR_7$ or $C_6R_{2-6}$—$CHR_1$—$COOR_7$ where $R_1$ is a hydrogen atom or an alkyl group, at least one of $R_2$, $R_3$, $R_4$, $R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom, and $R_7$ is a substituted or unsubstituted phenylene or naphthylene group dissolved in an organic solvent, irradiating the resist layer selectively with a radiation ray, and developing a portion irradiated by the ray to form a pattern of the resist layer.

5 Claims, 8 Drawing Sheets

PHOTOSENSITIVE COMPOUND, PHOTOSENSITIVE COMPOSITION, METHOD FOR RESIST PATTERN FORMATION, AND PROCESS FOR DEVICE PRODUCTION

BACKGROUND OF THE INVENTION

1. Field of the Invention

The present invention relates to a photosensitive compound, a photosensitive composition containing the photosensitive compound dissolved in a solvent, a method for resist pattern formation by use of the photosensitive composition, and a process for producing a device by the method for the resist pattern formation.

2. Description of the Related Art

In recent years, for fine working in semiconductor and other electronic device industries, higher density and higher integration in the devices are required. In the semiconductor device production process, photolithography is an important technique in fine pattern formation.

The photolithography employs essentially a technique for stable fine working to a precision of 100 nm or finer. Therefore, the resist used in the photolithography should enable formation of a pattern to a precision of 100 nm or finer.

Diazonaphthoquinone-novolak type resists are widely used. These resists utilize a dissolution inhibition effect of the diazonaphthoquinone compound on a phenol resin (U.S. Pat. No. 4,859,563).

A diazonaphthoquinone-novolak type resist constituted of a low-molecular phenol resin cannot be affected by the dissolution inhibition effect of the naphthoquinone compound, resulting in a low development contrast between exposed regions and unexposed regions.

Lately, chemically amplified resists are used as a high-resolution resist rather than the diazonaphthoquinone-novolak type resist. In the chemically amplified resist, an acid ($H^+$) is generated by irradiation with an active ray, and the generated acid catalyzes the deprotection reaction of an alkali-solubilizing group protected by an acid-decomposable protecting group to make the resist soluble in alkali (Journal of Photopolymer Science and Technology 17, 435, (2004)).

In formation of a resist pattern of a chemically amplified resist, the resist is heat-treated prior to the development in order to accelerate the deprotection reaction catalyzed by the acid generated in the exposed region.

In this heat treatment, the acid is allowed to diffuse to a distance of about 10 nm by the heat ("Proc. SPIE", 6154, 710, 2006). This diffusion of the acid causes fine roughness at the edge portions of the pattern, namely line edge roughness (LER), to lower the resolution.

The LER depends also on the molecular weight of the base compound. The base compound herein denotes a compound having an alkali-solubilizing group or a protected alkali-solubilizing group in the resist composition.

Since the base compound dissolves, molecule by molecule, into the developing solution, a larger molecular weight of the base compound causes larger LER.

A base compound of a lower molecular weight has a lower glass transition temperature and a lower melting point. When the chemically amplified resist is heated before the development treatment at a temperature higher than its glass transition temperature, the formed acid diffuses to a longer distance to lower the resolution.

Therefore, the base compound of the chemically amplified resist should have a glass transition temperature higher than the deprotection reaction temperature under acid catalysis. This requirement limits the design of the chemically amplified resist for a lower LER (line edge roughness) by use of a lower molecular-weight resist.

The inventors of the present invention found that, in a pattern formation by near-field light exposure, when a chemically amplified resist diluted with an organic solvent is applied in a thickness of 10 nm, the LER of the resulting resist pattern is larger undesirably.

J. Org. Chem. 2003, 68, 9100 (2003) discloses a caged compound having a latent physiological activity formed by nitrobenzyl-etherifying the phenolic hydroxyl group of capsaicin. This compound is not intended for use as a pattern-forming material.

J. Appl. Polym. Sci., 33, 1763 (1987) discloses a photosensitive polyimide resist having a nitrobenzyl group. This resist can be made alkali-soluble by light irradiation to eliminate the nitrobenzyl from the polyimide. The polymer of this resist is solubilized by elimination of the nitrobenzyl to form a carboxylic acid group (COOH). However, this resist gives resolution of as low as a micrometer order owing to swelling of the resist polymer caused by the reaction of the carboxylic acid with the alkali developing solution.

SUMMARY OF THE INVENTION

The present invention is directed to a photosensitive compound having, in the molecule, two or more structural units represented by General Formula (1):

where $R_1$ is a hydrogen atom or an alkyl group; at least one of $R_2$, $R_3$, $R_4$, $R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom; and $R_7$ is a substituted or unsubstituted phenylene or naphthylene group.

The photosensitive compound can have two or more structural units represented by General Formula (2) in the molecule:

The photosensitive compound can have two or more structural units represented by General Formula (3) in the molecule:

(3)

The photosensitive compound can have two or more structural units represented by General Formula (4) in the molecule:

(4)

The photosensitive compound can have two or more structural units represented by General Formula (5) in the molecule:

(5)

The present invention is directed to a photosensitive compound having, in the molecule, two or more structural units represented by General Formula (6):

(6)

where $R_1$ is a hydrogen atom or an alkyl group; at least one of $R_2, R_3, R_4, R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom; and $R_7$ is a substituted or unsubstituted phenylene or naphthylene group.

The photosensitive compound has two or more structural units represented by General Formula (7) in the molecule:

(7)

The photosensitive compound can have two or more structural units represented by General Formula (8) in the molecule:

(8)

The photosensitive can have two or more structural units represented by General Formula (9) in the molecule:

(9)

The photosensitive compound can have two or more structural units represented by General Formula (10) in the molecule:

(10)

The present invention is directed to a poly(hydroxystyrene) in which hydrogen atoms of two or more hydroxyl groups are substituted by the substituent represented by General Formula (11) or (12):

(11)

-continued (12)

where $R_1$ is a hydrogen atom or an alkyl group; at least one of $R_2$, $R_3$, $R_4$, $R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom.

The present invention is directed to a calixarene in which hydrogen atoms of two or more phenolic hydroxyl groups are substituted by the substituent represented by General Formula (11) or (12):

(11)

(12)

where $R_1$ is a hydrogen atom or an alkyl group; at least one of $R_2$, $R_3$, $R_4$, $R_5$, and $R_6$ is a nitro group, and other are selected from the group consisting of a hydrogen atom, a halogen atom, an alkyl, an alkoxy, a phenyl, a naphthyl, and an alkyl in which a part or the entire of hydrogen atoms are substituted by a fluorine atom.

The present invention is directed to a novolak resin in which in which hydrogen atoms of two or more phenolic hydroxyl groups are substituted by the substituent represented by General Formula (11) or (12):

(11)

(12)

where $R_1$ is a hydrogen atom or an alkyl group; at least one of $R_2$, $R_3$, $R_4$, $R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom.

The present invention is directed to a photosensitive composition comprising at least one of the compounds set forth above dissolved in an organic solvent.

The present invention is directed to a process for forming a resist pattern comprising the steps of: applying the photosensitive composition set forth above on a substrate to form a photosensitive resist layer, irradiating the resist layer selectively with a radiation ray, and developing a portion irradiated by the ray to form a pattern of the resist layer.

In the process for forming a resist pattern, a resist layer capable of being removed by plasma etching and another resist layer resistant to plasma etching can be laminated, and the photosensitive resist layer can be formed on the layer resistant to plasma etching.

In the process for forming a resist pattern, the photosensitive resist layer can be formed in a thickness not more than 20 nm.

In the process for forming a resist pattern, the irradiation of the radiation ray can be conducted with near-field light.

The present invention is directed to a process for producing a device, in which the device is formed on a substrate by the process for forming a resist pattern set forth above.

The photosensitive compound of the present invention need not be heated after the light exposure in resist pattern formation. Therefore, a lower-molecular phenol compound can be used without heating regardless of the restriction in the glass-transition temperature and melting point in the present invention. The photosensitive compound of the present invention enables formation of a resist pattern with a low LER.

Further features of the present invention will become apparent from the following description of exemplary embodiments with reference to the attached drawings.

DESCRIPTION OF THE EMBODIMENTS

The present invention provides a photosensitive compound for formation of a resist pattern having a low LER (line edge roughness) even with a small film thickness, a photosensitive composition containing the photosensitive compound, a method of formation of a resist pattern, and a process for producing a device.

In the present invention, the LER is defined to be three times the standard deviation (3σ) of the line pattern breadth. For estimation of the LER, line breadths are measured at 50 or more points sampled in a line pattern of 0.5 to 2 μm long at constant intervals of 10 nm along line length. The LER is calculated from the measured line breadths as the population. The breadth is measured by scanning electron microscopy, atomic force microscopy, or the like.

The photosensitive compound of the present invention containing two or more structure units represented by aforementioned General Formula (1) or (6) can be synthesized through a known condensation reaction of a nitrobenzyl alcohol derivative represented by Formula (21) or (22) below with a compound containing two or more phenolic hydroxyl groups in the molecule (hereinafter referred to as "a polyphenolic compound").

(21)

wherein $R_1$ to $R_6$ are as defined before, and X is a hydroxyl group or a halogen atom.

(22)

wherein $R_1$ to $R_6$ are as defined before, and Y is a hydroxyl or a halogen atom.

The polyphenolic compounds used in the above condensation reaction are roughly classified into polymer compounds, compounds having a molecular weight of not higher than 2000, and low-molecular compounds constituted of one or more monomers. The polyphenolic compound is preferably a low-molecular compound, or a polymer compound having a weight-average molecular weight (Mw) ranging from 1000 to 100000, more preferably from 3000 to 50000 and having molecular weight distribution (Mw/Mn) ranging from 1.0 to 3.0, preferably from 1.0 to 1.5, more preferably from 1.0 to 1.2. The narrower molecular weight distribution gives smaller LER (line edge roughness). Particularly preferred are hydroxystyrene homopolymers having a weight-average molecular weight ranging from 3000 to 50000 and a molecular weight distribution ranging from 1.0 to 1.2.

Through the above condensation reaction, the phenol group or groups are nitrobenzyl-etherified or nitrobenzyl-carbonated to give the unit structure represented by General Formula (1) or (6).

In the above condensation reaction, not all of the phenol groups in the polyphenolic compound may be nitrobenzyl-etherified or nitrobenzyl-carbonated. Two or more of the phenol groups in the molecule are preferably nitrobenzyl-etherified or nitrobenzyl-carbonated, and the nitrobenzyl-etherification degree or the nitrobenzyl-carbonation degree is preferably in the range from 10% to 90%, more preferably from 10% to 50%. A higher degree of the nitrobenzyl-etherification or nitrobenzyl-carbonation than 90% necessitates a larger quantity of exposure light for the resist pattern formation, and lowers the adhesiveness of the resist onto the worked substrate owing to the lowered polarity. A lower degree of the nitrobenzyl-etherification than 10% lowers resistance of the resist pattern against the developer solution.

The condensation reaction can be allowed to proceed through a known process such as a method described in J. Org. Chem. 68, 9100 (2003) or a method described in J. Am. Chem. Soc, 110, 301, (1988).

The compound represented by Formula (21) includes specifically compounds below: 2-nitrobenzyl alcohol, 2-nitrobenzyl chloride, 2-nitrobenzyl bromide, 2-methyl-2-nitrobenzyl alcohol, 2-methyl-2-nitrobenzyl chloride, 2-methyl-2-nitrobenzyl bromide, 3-methyl-2-nitrobenzyl alcohol, 3-methyl-2-nitrobenzyl chloride, 3-methyl-2-nitrobenzyl bromide, 5-methyl-2-nitrobenzyl alcohol, 5-methyl-2-nitrobenzyl chloride, 5-methyl-2-nitrobenzyl bromide, 3-chloro-2-nitrobenzyl alcohol, 3-chloro-2-nitrobenzyl chloride, 3-chloro-2-nitrobenzyl bromide, 4-chloro-2-nitrobenzyl alcohol, 4-chloro-2-nitrobenzyl chloride, 4-chloro-2-nitrobenzyl bromide, 5-chloro-2-nitrobenzyl alcohol, 5-chloro-2-nitrobenzyl chloride, 5-chloro-2-nitrobenzyl bromide, 4,5-dimethoxy-2-nitrobenzyl alcohol, 4,5-dimethoxy-2-nitrobenzyl chloride, 4,5-dimethoxy-2-nitrobenzyl bromide, 5-(3-iodopropoxy)-2-nitrobenzyl alcohol, 5-(3-iodopropoxy)-2-nitrobenzyl chloride, and 5-(3-iodopropoxy)-2-nitrobenzyl bromide.

The compound represented by Formula (22) includes specifically compounds below: 2-nitrobenzyl formate, 2-nitrobenzyl chloroformate, 2-nitrobenzyl bromoformate, 2-methyl-2-nitrobenzyl formate, 2-methyl-2-nitrobenzyl chloroformate, 2-methyl-2-nitrobenzyl bromoformate, 3-methyl-2-nitrobenzyl formate, 3-methyl-2-nitrobenzyl chloroformate, 3-methyl-2-nitrobenzyl bromoformate, 5-methyl-2-nitrobenzyl formate, 5-methyl-2-nitrobenzyl chloroformate, 5-methyl-2-nitrobenzyl bromoformate, 3-chloro-2-nitrobenzyl formate, 3-chloro-2-nitrobenzyl chloroformate, 3-chloro-2-nitrobenzyl bromoformate, 4-chloro-2-nitrobenzyl formate, 4-chloro-2-nitrobenzyl chloroformate, 4-chloro-2-nitrobenzyl bromoformate, 5-chloro-2-nitrobenzyl formate, 5-chloro-2-nitrobenzyl chloroformate, 5-chloro-2-nitrobenzyl bromoformate, 4,5-dimethoxy-2-nitrobenzyl formate, 4,5-dimethoxy-2-nitrobenzyl chloroformate, 4,5-dimethoxy-2-nitrobenzyl bromoformate, 5-(3-iodopropoxy)-2-nitrobenzyl formate, 5-(3-iodopropoxy)-2-nitrobenzyl chloroformate, and 5-(3-iodopropoxy)-2-nitrobenzyl bromoformate.

The high-molecular polyphenolic compound is exemplified by condensation reaction products of a phenol and an aldehyde, condensation products of a phenol and a ketone, vinylphenol type polymers, such as poly(hydroxystyrene), and isopropenylphenol type polymers.

The ketone includes acetone, methyl ethyl ketone, diethyl ketone, and diphenyl ketone.

The phenol includes a monohydric phenols such as phenol, cresol, xylenol, ethylphenol, propylphenol, butylphenol, and phenylphenol; polyhydric phenols such as resorcinol, pyrocatecol, hydroquinone, bisphenol-A, and pyrogallol.

The aldehyde includes formaldehyde, acetaldehyde, benzaldehyde, and terephthalaldehyde.

The ketone includes acetone, methyl ethyl ketone, diethyl ketone, and diphenyl ketone.

The condensation reaction of the phenol with the aldehyde can be conducted by a conventional method. The condensation reaction product of the phenol and the aldehyde is exemplified by phenol-novolak resins, cresol-novolak resins, and calixarenes. Through a condensation reaction by use of such a novolak resin or a calixarene as the high-molecular polyphenolic compound, the hydrogen atoms of two or more of the phenolic hydroxyl groups thereof are substituted by the substituent represented by the above Formula (11) or (12) to form a novolak resin or a calixarene of the present invention.

The vinylphenol type polymer is selected from homopolymers of vinylphenol (hydroxystyrene) and copolymers thereof with a copolymerizable component. The copolymerizable component includes acrylic acid, methacrylic acid, styrene, maleic anhydride, maleimide, vinyl acetate, and acrylonitrile; and derivatives thereof.

The isopropenylphenol type polymer is selected from homopolymers of isopropenylphenol and copolymers thereof with a copolymerizable component. The copolymerizable component includes acrylic acid, methacrylic acid, styrene, maleic anhydride, maleimide, vinyl acetate, and acrylonitrile; and derivatives thereof.

The low molecular polyphenolic compound includes calixarene derivatives and compounds represented by Formulas (31) to (36) below:

(31)

where $R_{31}$ is an alkyl group of 1-4 carbon atoms, a phenyl group, or a 1-naphthyl group; a plurality of $R_{31}$ may be the same or different; p is an integer of 1 or more, q is 0 or an integer, and $p+q \leq 6$.

(32)

where the symbols denote the same as in Formula (31); Z is a single bond, —S—, —O—, —CO—, —COO—, —SO—, —SO$_2$—, or —C(R$_{32}$)$_2$— (where $R_{32}$ is a hydrogen atom, an alkyl group of 1-6 carbon atoms, an acyl group of 2-11 carbon atoms, a phenyl group, or a naphthyl group, and plural $R_{32}$ may be the same or different from each other), or the group represented by Formula (33) below:

(33)

(where $R_{31}$ is the same as in Formula (31); t is an integer of 0-4)

(34)

wherein $R_{31}$ is the same as in Formula (31), and $R_{32}$ is the same as in Formula (32); p, q, r, s, u, and v are, respectively, an integer of 0 or more; and $p+q \leq 5$, $r+s \leq 5$, $u+v \leq 5$, and $p+r+u \geq 1$.

(35)

wherein $R_{31}$ is the same as in Formula (31); $R_{32}$ and Z are the same as in Formula (32); plural $R_{31}$ are the same or different from each other; plural $R_{32}$ are the same or different from each other; p, q, r, s, u, v, w, and x are, respectively, an integer of 0 or more; and $p+q \leq 5$, $r+s \leq 5$, $u+v \leq 5$, $w+x \leq 5$, and $p+r+u+w \geq 1$.

(36)

wherein $R_{31}$ is the same as in Formula (31); $R_{32}$ is the same as in Formula (32); plural $R_{31}$ are the same or different from each other; plural $R_{32}$ are the same or different from each other; p, q, r, s, u, v, w, and x area, respectively, an integer of 0 or more; and $p+q \leqq 5$, $r+s \leqq 5$, $u+v \leqq 5$, $w+x \leqq 4$, and $p+r+u+w \geqq 1$.

The photosensitive compound of the present invention produces a phenolic hydroxyl group, an alkali-solubilizing group, directly through a photochemical reaction as shown in Reaction Formula (1) or (2). Thus the photosensitive compound functions as a positive resist: a light-exposed portion thereof is dissolved by a developer solution.

Reaction Formula (1) shows the process of the photochemical reaction of nitrobenzyl phenyl ether, and Reaction Formula (2) shows the process of the photochemical reaction of nitrobenzyl phenyl carbonate.

Reaction Formula (1)

Reaction Formula (2):

The photosensitive compound of the present invention may be dissolved in a solvent at a solid concentration ranging from 2% to 50% by weight for use as a photosensitive composition. The photosensitive composition is preferably filtered through a filter of pore diameter of about 0.1 to 0.2 μm.

The above-mentioned solvent is not limited specially and can be selected arbitrarily, insofar as the solvent is capable of dissolving the photosensitive compound and will not react with the photosensitive compound. The solvent may be a simple solvent, or a mixture of solvents. The solvent includes ethers, esters, ether esters, ketones, ketone esters, amides, amide esters, lactams, lactones, hydrocarbons, and halogenated hydrocarbons. More specifically, the solvent includes ethylene glycol monoalkyl ethers, diethylene glycol dialkyl ethers, ethylene glycol monoalkyl ether acetates, propylene glycol monoalkyl ether acetates, propylene glycol monoalkyl ethers, propylene glycol dialkyl ethers, acetate esters, hydroxyacetate esters, lactate esters, alkoxyacetate esters, cyclic or acyclic ketones, acetoacetate esters, pyruvate esters, propionate esters, N,N-dialkylformamides, N,N-dialkylacetamides, N-alkylpyrrolidones, γ-lactones, (halogenated) aliphatic hydrocarbons, and (halogenated) aromatic hydrocarbons.

Still more specifically, examples of the solvents are as follows: ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether acetate (PGMEA), propylene glycol monoethyl ether acetate, propylene glycol mono-n-propyl ether acetate, isopropenyl acetate, isopropenyl propionate, toluene, xylene, methyl ethyl ketone, cyclohexanone, 2-heptanone, 3-heptanone, 4-heptanone, ethyl 2-hydroxypropionate, ethyl 2-hydroxy-2-methylpropionate, ethyl ethoxyacetate, ethyl hydroxyacetate, methyl 2-hydroxy-3-methylbutyrate, 3-methoxybutyl acetate, 3-methyl-3-methoxybutyl acetate, 3-methyl-3-methoxybutyl propionate, 3-methyl-3-methoxybutyl butyrate, ethyl acetate, n-propyl acetate, n-butyl acetate, methyl acetoacetate, ethyl acetoacetate, methyl 3-methoxypropionate, ethyl 3-methoxypropionate, methyl 3-ethoxypropionate, ethyl 3-ethoxypropionate, N-methylpyrrolidone, N,N-dimethylformamide, and N,N-dimethylacetamide.

In consideration of safety, preferred are propylene glycol monomethyl ether acetate (PGMEA), ethyl-2-hydroxypropionate, and cyclohexanone.

The above-mentioned solvent may contain one or more high-boiling solvents as necessary. The high-boiling solvent includes benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and ethylene glycol monophenyl ether acetate.

The photosensitive composition of the present invention may contain a surfactant at a content of not more than 0.2 part by weight based on the total weight (100 parts) of the photosensitive compound, preferably ranging from 0.001 to 0.05 part, more preferably from 0.003 to 0.02 part by weight.

The surfactant includes fluorine type surfactants; silicone type surfactants; polyoxyethylene alkyl ethers such as polyoxyethylene lauryl ether, polyoxyethylene stearyl ether, and polyoxyethylene oleyl ether; polyoxyethylene aryl ethers such as polyoxyethylene octyl phenyl ether, and polyoxyethylene nonyl phenyl ether; polyoxyethylene dialkyl esters such as polyoxyethylene dilaurate, and polyoxyethylene distearate.

Commercially available surfactants include BM-1000, and BM-1100 (BM Chemie Co.); Megafack F142D, F144D, F171, F172, F173, F177, F178A, F178K, F179, F183, F184, and F191 (Dainippon Ink & Chemicals Inc.); Florard FC-135, FC-170C, FC-171, FC-176, FC-430, and FC-431; Megafack RS-1, RS-7, RS-9, RS-15, and R-08 (Sumitomo 3M Ltd.); Sufflon S-112, S-113, S-131, S-141, S-145, S-382, SC-101, SC-102, SC-103, SC-104, SC-105, and SC-106 (Asahi Glass Co.); F-Top EF301, EF303, and EF 352 (Shin Akita Kasei K.K.); SH-28PA, SH-190, SH-193, SZ-6032, SF-8428, DC-57, and DC-190 (Dow Coming Toray Silicone Co.); Organosiloxane Polymer KP341 (Shin-Etsu Chemical Co.); methacrylate type copolymers Polyflow No. 57, No. 95 (Kyoeisha Kagaku K.K.); Ftargent FT-250, FT-251, and FTX-218 (Neosu K.K.).

The photosensitive composition may contain further a known additive such as a colorant, an auxiliary adhesive, a storage stabilizer, and a defoaming agent.

A solution of the photosensitive composition of the present invention can be applied by a known application apparatus such as a spin coater, a dip coater, and a roller coater by a known method. The applied film has usually a thickness ranging from 0.01 to 5 μm after prebaking, depending on the use thereof.

The material of the substrate for the photosensitive composition includes metals, semiconductors, glass, quartz, BN, and organic materials. The substrate may be coated with a film or films of a resist, a spin-on-glass material, an organic substance, a metal, an oxide, a nitride, or the like.

The substrate coated with plural kinds of coating films is exemplified by a substrate coated with a lamination of a resist layer susceptible to plasma etching and another resist layer resistant to plasma etching. A preferred example is a substrate which is coated with an underlayer of a resist susceptible to oxygen dry-etching and a layer resistant to oxygen plasma etching formed in the named order.

The resist for the underlayer includes thermosetting phenol resins, but is not limited thereto.

The oxygen-plasma-resistant layer may be formed from $SiO_2$, $TiO_2$, or a spin-on-glass material, but is not limited thereto.

The resist underlayer is formed in a thickness ranging preferably from 0.01 to 1 μm. The layer resistant to oxygen plasma etching is formed in a thickness ranging preferably from 0.001 to 1 μm.

The applied coating film of the photosensitive composition is prebaked suitably, depending on the boiling point of the solvent or other properties of the photosensitive composition, at a temperature ranging from 50° C. to 150° C., preferably from 80° C. to 110° C. The prebaking can be conducted by a hot-plate, a hot-air drier, or a like heating means.

For pattern formation, the applied photosensitive composition layer is exposed to imagewise irradiation selectively through a mask by a known exposure system. The irradiation ray for the exposure includes visible rays, ultraviolet rays, far ultraviolet rays, X-rays, electron rays, γ-rays, molecular beams, and ion beams. The ray is selected suitably. Preferred are mercury lamp beams (wavelengths: 436 nm, 365 nm, 254 nm), a KrF excimer laser beam (wavelength: 248 nm), an ArF excimer laser beam (wavelength: 193 nm), a F2 excimer laser beam (wavelength: 157 nm), far ultraviolet beams such as an extreme ultraviolet beam (EUV, wavelength: 13 nm), and electron beams. One or more of irradiation rays may be employed.

Otherwise, the exposure may be conducted by near-field light which is generated by a photomask having a light absorber having an aperture breadth smaller than the wavelength of exposure light source. For the near-field light exposure, the above-mentioned irradiation rays are useful. The irradiation may be conducted with a single beam or two or more kinds of beams in combination. The near-field exposure is conducted by bringing the light absorber close to the irradiation object so that the near-field light may reach the irradiation object (for instance, close contact with the object).

For finer resist pattern, particularly preferred for the exposure are shorter wavelength beams such as ArF excimer laser beams, F2 excimer laser beams, EUV beams, electron beams, and near-field light which is not affected by diffraction limit.

Figure 1:
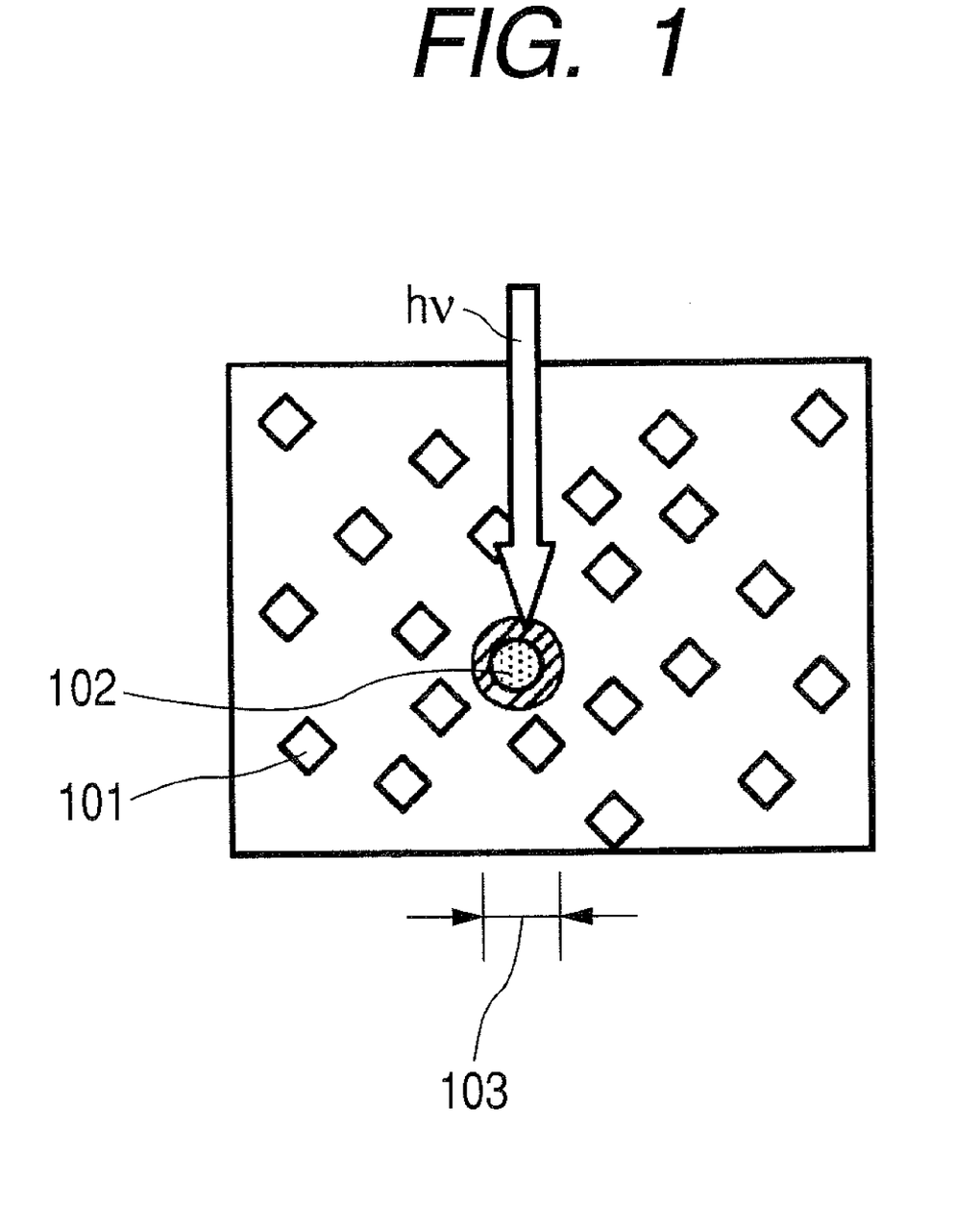
FIG. 1 is a drawing for describing the photochemical reaction of the photosensitive compound of the present invention.
Figure 2A:
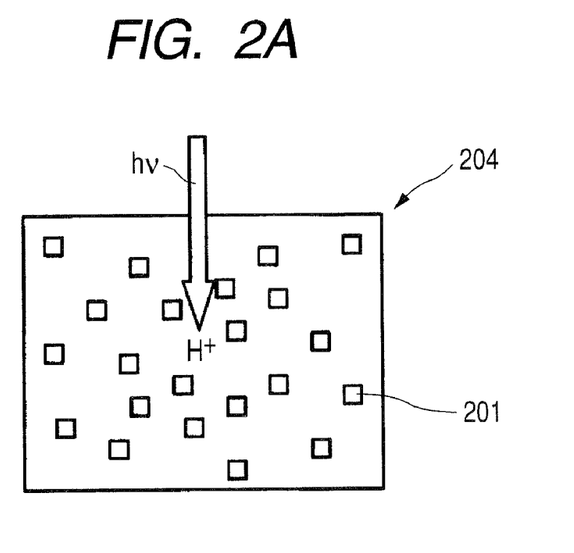
FIGS. 2A and 2B are drawings for describing a photochemical reaction of a conventional chemically amplified resist.
Figure 2B:
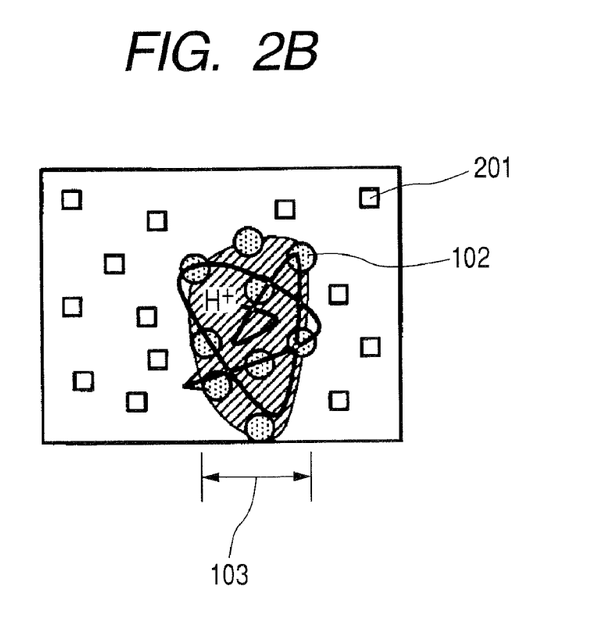

The photochemical reaction of the photosensitive composition of the present invention is different from that of conventional chemically amplified resist as described below. In FIGS. 1 and 2B, the region in which one photon can induce a deprotection reaction is defined as photoreaction spot 103. In conventional methods, one photon hv introduced into resist layer 204 produces one molecule of an acid: the acid as a catalyst diffuses by promotion by the heat given before the development to induce deprotection reaction of plural alkali-solubilizing groups 201 protected by an acid-decomposable protecting group to give plural alkali-solubilizing groups 102. Therefore, one photoreaction spot in the chemically amplified resist has a size of about 10 nm. On the other hand, in the present invention, the heat treatment before the development is not necessary, so that one photon induces deprotection of one group in a molecule of the photosensitive compound of the present invention. In other words, one photon hv introduced into the resist layer produces one free alkali-solubilizing group 102 from one alkali-solubilizing group 101 protected by a photo-decomposable protecting group. Therefore, the photoreaction spot in the present invention has a size of a molecular scale (ranging from 0.1 to 1 nm). This enables decrease of LER of a resist pattern.

After the exposure, the exposed portion (irradiated portion) of the photosensitive resist layer is developed and removed, and the resist is washed and dried to obtain an intended resist pattern.

For the development, an aqueous alkaline solution containing the compound exemplified below is used as the developer solution: sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, and 1,5-diazabicyclo[4.3.0]-5-nonene. The developer solution may contain a water-soluble organic solvent such as methanol, and ethanol, or a surfactant in a suitable amount. An aqueous 2.38-wt % tetramethylammonium hydroxide solution is particularly preferred.

The development is conducted by dipping, spraying, brushing, slapping, or a like method.

In the case where the resist pattern film is formed on a substrate having an underlying resist layer and an oxygen plasma-resistant layer formed thereon in this order, firstly the oxygen plasma-resistant layer is etched through the above-mentioned resist pattern as the mask. The etching may be conducted either by wet etching or by dry etching. The dry etching is suitable for fine pattern formation and is preferred. The etchant for the wet etching is selected depending on the etching object, including aqueous fluoric acid solutions, aqueous ammonium fluoride solutions, aqueous phosphoric acid solutions, aqueous acetic acid solutions, aqueous nitric acid solutions, and aqueous cerium ammonium nitrate solutions. The gas for dry etching includes $CHF_3$, $CF_4$, $C_2F_6$, $SF_6$, $CCl_4$, $BCl_3$, $Cl_2$, HCl, $H_2$, and Ar, and mixtures thereof.

Next, oxygen plasma etching is conducted through the patterned oxygen plasma-resistant layer as the mask. The oxygen-containing gas for the oxygen plasma etching includes simple oxygen, mixtures of oxygen with an inert gas such as argon, mixtures of oxygen with carbon monoxide, carbon dioxide, ammonia, dinitrogen monoxide, or sulfur dioxide.

Through the above two-step etching, a resist pattern can be obtained which has a higher aspect ratio than the resist pattern formed by exposure and development.

With the resist pattern formed as above as the mask, a substrate such as a semiconductor substrate of silicon, germanium, or the like is dry-etched or wet-etched. The substrate is further worked by metal vapor deposition, lift-off, plating, and so forth to form an intended device on the substrate. For instance, a semiconductor device can be prepared as described below.

Firstly, a device circuit of a semiconductor is designed. Then a mask is prepared which has a circuit pattern corresponding to the intended circuit. Separately, a substrate for the device is prepared, and thereon the photosensitive composition of the present invention is laminated.

Then, the circuit is formed on the substrate by lithography with the mask and a conventional exposure system. The process for formation of the circuit includes oxide film formation, etching, insulation film formation, conductive wiring film formation, and patterning. Next, the substrate having the circuit is subjected to an assembly process (dicing, and bonding), packaging, and so forth, and is chipped.

EXAMPLES

The present invention is described specifically by reference to Examples.

Example 1

Synthesis of Photosensitive Compounds

In a 100-mL reactor, 4.0 g of poly(hydroxystyrene) (PHS) (33.3 mmol in terms of hydroxystyrene monomer, defined as 1.0 mol-equivalent) was dissolved in 40 mL of N,N-dimethylformamide. The poly(hydroxystyrene) (PHS) had a weight-average molecular weight (Mw) of 4100, and a molecular weight distribution (Mw/Mn) of 1.1.

To this solution, was added 0.21 g of sodium hydride (8.75 mmol, 0.265 mol-equivalent) at room temperature (23° C.), and the mixture was stirred for 30 minutes, and further at 50° C. for two hours.

To this liquid suspension, was added 2.15 g (7.8 mmol, 0.235 mol-equivalent) of 4,5-dimethoxy-2-nitrobenzyl bromide at one time, and the mixture was stirred at 50° C. for one hour.

To this solution, was added again 0.21 g (8.75 mmol, 0.265 mol-equivalent) of sodium hydride, and the mixture was stirred for one hour.

Then, to this liquid suspension, was added 2.15 g (7.8 mmol, 0.235 mol-equivalent) of 4,5-dimethoxy-2-nitrobenzyl bromide at one time, and the mixture was stirred at 50° C. for two hours.

The resulting solution was stirred at room temperature without heating for 18 hours.

To this solution, was added 100 mL of an aqueous 10% ammonium chloride solution. The aqueous phase was extracted with 100 mL of ethyl acetate three times. The organic phase portions were combined, and the combined organic phase was washed with 100 mL of water eight times and 100 mL of saturated sodium chloride solution once. The washed organic phase was dried over anhydrous magnesium sulfate, and was concentrated.

Toluene was added to this solution to precipitate the intended polymer. The supernatant liquid was removed, and toluene was added again thereto, and the polymer was suspended. After left standing, the supernatant was removed.

The viscous polymer was dissolved in 80 mL of ethyl acetate. The solution was added slowly dropwise into 1.2 L of hexane. The reprecipitated crystal was washed with hexane, and dried under a high vacuum to obtain pale yellow solid of photosensitive compound A (nitrobenzyl ether group introduction degree: 38%).

Reaction Formula (3) below shows the pathway of the synthesis of photosensitive compound A:

where m and n are both an integer of 0 or more.

Through the same synthetic pathway as above of Photosensitive Compound A, synthesis was conducted by changing the amounts of addition of sodium hydride and 4,5-dimethoxy-2-nitrobenzyl bromide to obtain photosensitive compounds. As the results, were obtained Photosensitive Compound B (nitrobenzyl ether group introduction degree: 26%), Photosensitive Compound C (nitrobenzyl ether group introduction degree: 20%), and Photosensitive Compound D (nitrobenzyl ether group introduction degree: 16%).

Example 2

Preparation of Photosensitive Compositions

The Photosensitive Compounds A to D were dissolved respectively in propylene glycol monomethyl ether acetate (PGMEA) at a concentration of 10 wt % to obtain Photosensitive Compositions A' to D'.

Photosensitive Compounds A to D were dissolved respectively in PGMEA at a concentration of 1.25 wt % to obtain Photosensitive Compositions A" to D".

Example 3

Evaluation of Photosensitive Compounds for Resistance to Developer Solution

Photosensitive compounds A' to D' and a 10-wt % PHS solution in PGMEA (PHS having a weight-average molecular weight (Mw) or 4100 and a molecular weight distribution (Mw/Mn) of 1.1) were respectively applied on Si substrates having been treated with hexamethyldisilazane (HMDS) by spin coating.

Then the substrates coated with the compositions were heated on a hot plate at 90° C. for 90 seconds to obtain five coating films of Photosensitive Compounds A-D and polyhydroxystyrene (PHS) formed on the substrates.

The five substrates were immersed in an aqueous 2.38-wt % tetramethylammonium hydroxide solution. The film thicknesses were measured before and after the immersion by a spectroscopic ellipsometer to estimate the speed of dissolution (nm/s) into the developer solution.

Figure 3:
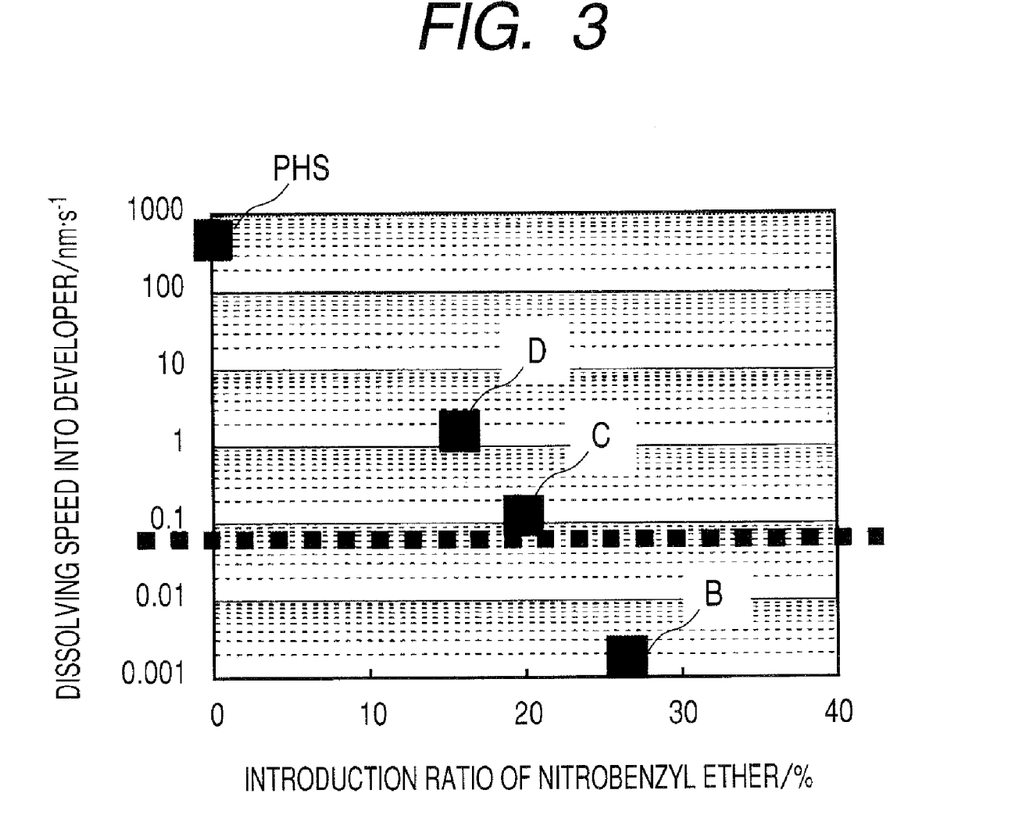
FIG. 3 illustrates dependence of the speed of dissolution of the photosensitive compound into a developer solution on the ratio of nitrobenzyl ether introduction in the photosensitive compound.

FIG. 3 shows dependence of the dissolution speed into the developer solution on nitrobenzyl ether introduction degree of the photosensitive compound. Photosensitive Compound A (nitrobenzyl ether introduction degree: 38%) dissolved at a dissolution speed of less than 0.001 nm/s, the speed being outside FIG. 3.

Generally, the speed of development of the unexposed portion of a positive resist is preferably not more than 0.1 nm/s. Therefore, Photosensitive Compositions A and B (nitrobenzyl ether introduction degree: 38%, 26%, respectively) were found to be useful as the positive resist.

The change of the film thickness of Photosensitive Compound A in the developer immersion test was less than the measurement limit of the spectroscopic ellipsometer, which prevents the measurement of the development velocity.

Example 4

Measurement of Extinction Coefficient of Photosensitive Compounds

Figure 4:
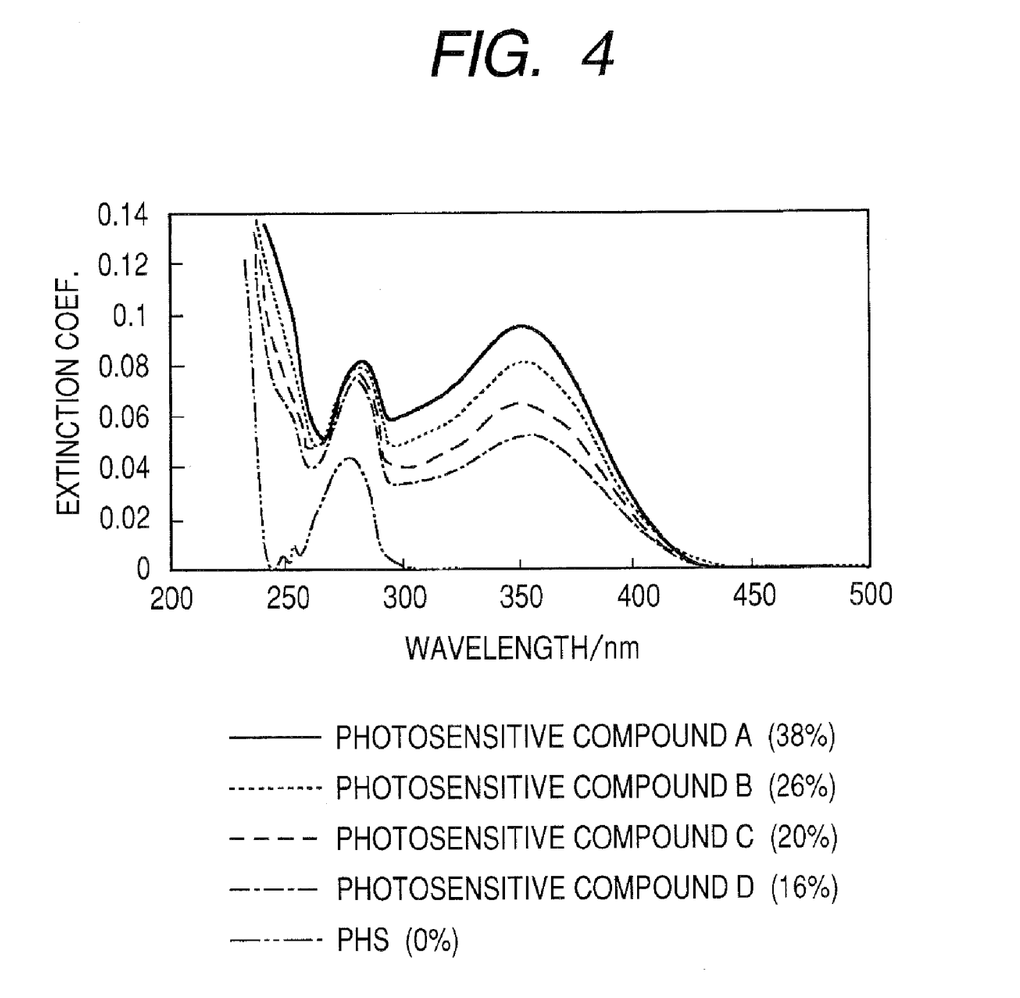
FIG. 4 illustrates extinction coefficients of coating films of photosensitive compounds A to D and PHS (polyhydroxystyrene) in Example 4 of the present invention.

The extinction coefficients of the coating films, formed in Example 3, of Photosensitive Compounds A-D were measured by a spectroscopic ellipsometer. FIG. 4 shows extinction coefficients of the coating films of Photosensitive Compounds A-D and PHS in the wavelength range from 200 nm to 500 nm. Photosensitive Compounds A-D were found to absorb light in the wavelength range below 420 nm.

Example 5

Formation of Resist Pattern by Near-Field Light Exposure (1)

On a Si substrate, a thermosetting phenol resin (AR2455, Rohm & Haas Co.) of 100 nm thick and a spin-on-glass material (T-03AS, Honeywell Co.) of 20 nm thick were laminated in this order by spin coating.

The surface of the spin-on-glass material layer was treated with hexamethyldisilazane (HMDS).

Photosensitive Composition M for comparison was prepared as described below. To 100 weight parts of a chemically amplified positive resist (TDUR-P308EM, Tokyo Ohka Co.) for KrF excimer laser exposure, composed of a poly(hydroxystyrene), was added 5 parts by weight of a photo acid generator (PAG) (CGI1397, Ciba Specialty Chemicals Co.). The mixture was diluted with propylene glycol monomethyl ether acetate (PGMEA) to prepare Photosensitive Composition M.

On the above-prepared substrate, Photosensitive Composition A" or Photosensitive Composition M was respectively applied by spin coating in a thickness after heating of 20 nm, and were heated on a hot plate at 90° C. for 90 seconds to prepare resist-coated substrates.

A photomask for near-field light exposure was prepared which is constituted of a patterned amorphous Si film of 50 nm thick as a light absorber and a supporting silicon nitride film (transparent substrate) of 400 nm thick, the patterned amorphous Si film having a line-and-space pattern of a pitch of 90 nm and a space breadth of about 30 nm. This photomask had a membrane structure: the light absorber and the silicon nitride film can be deformed elastically to be close to (e.g., to be contact with) a resist-coated substrate.

The photomask was placed in opposition to the resist-coated substrate to place the light absorber parallel to the substrate with a gap of 50 μm. The photomask was brought into immediate contact with the resist-coated substrate by deforming the membrane by applying a pressure from the transparent substrate side.

In this state, i-line light (wavelength: 365 nm, illuminance: 250 mW/cm$^2$) of an ultrahigh pressure mercury lamp was projected through an i-line band pass filter from the transparent substrate side. Since the opening space breadth is about 30 nm and is narrower than the wavelength of the projected light, propagation light is intercepted and only the near-field light (wavelength 365 nm) is introduced in the resist film kept in immediate contact with the light absorber.

Immediately after the near-field light exposure, the resist-coated substrate coated with Photosensitive Composition A" was immersed into an aqueous 2.38-wt % tetramethylammonium hydroxide solution for 10 seconds, and was rinsed with distilled water for 20 seconds to form a resist pattern of a pitch of 90 nm.

On the other hand, the resist-coated substrate coated with Photosensitive Composition M, after the near-field exposure, was heated on a hot plate at 110° C. for 90 seconds, and was immersed and rinsed in the same manner as above.

Figure 5A:
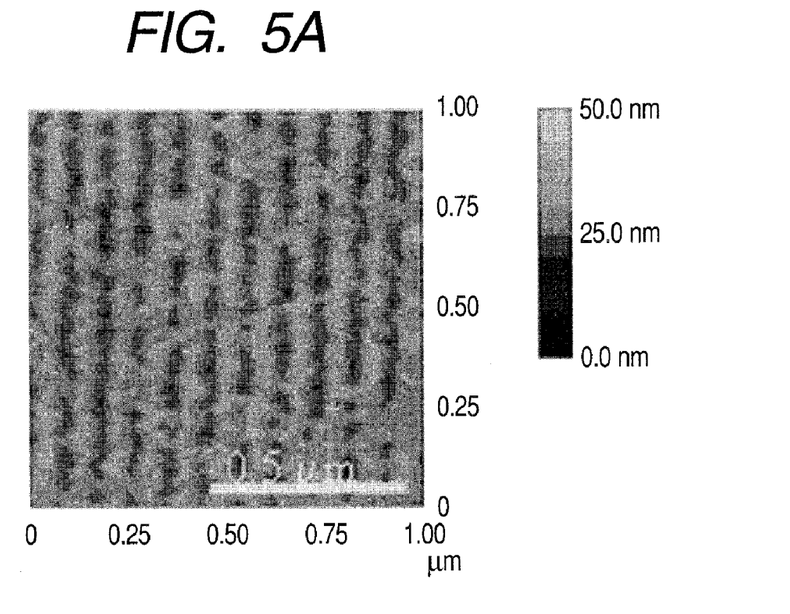
FIG. 5A is an atomic force photomicrograph of a resist pattern having a pitch of 90 nm employing photosensitive composition M.
Figure 5B:
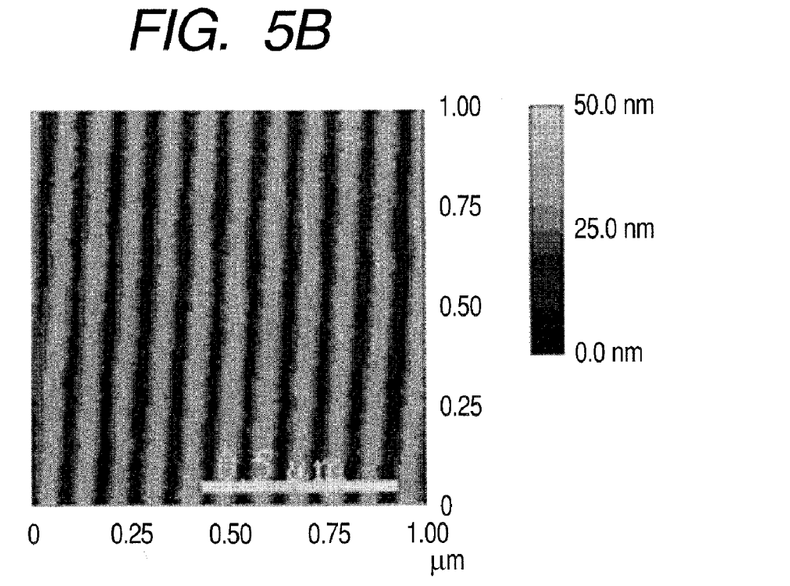
FIG. 5B is an atomic force photomicrograph of a resist pattern having a pitch of 90 nm employing photosensitive composition A.
Figure 6:
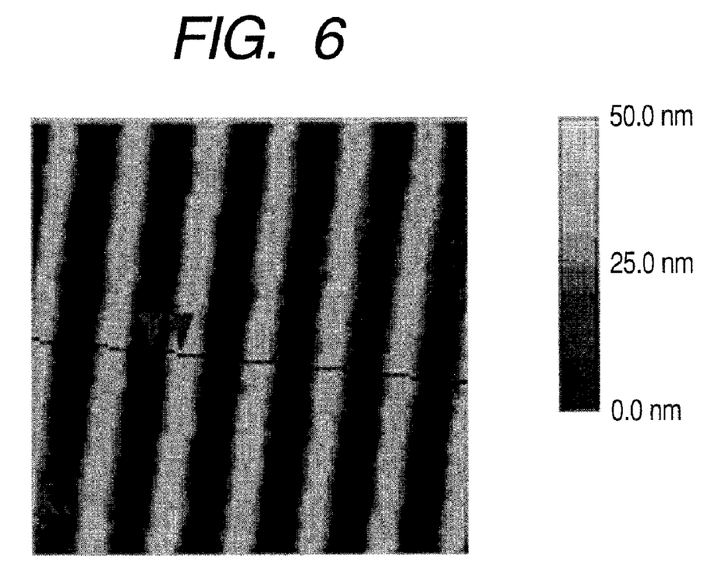
FIG. 6 is an atomic force photomicrograph of 1 μm² of a resist pattern having a film thickness of 30 nm and a pitch of 160 nm employing photosensitive composition M.
Figure 7:
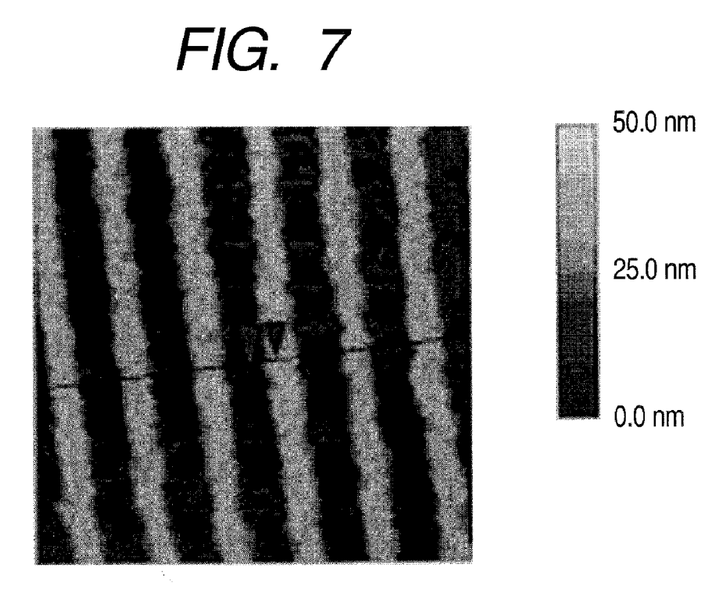
FIG. 7 is an atomic force photomicrograph of 1 μm² of a resist pattern having a film thickness of 20 nm and a pitch of 160 nm employing photosensitive composition M.
Figure 8:
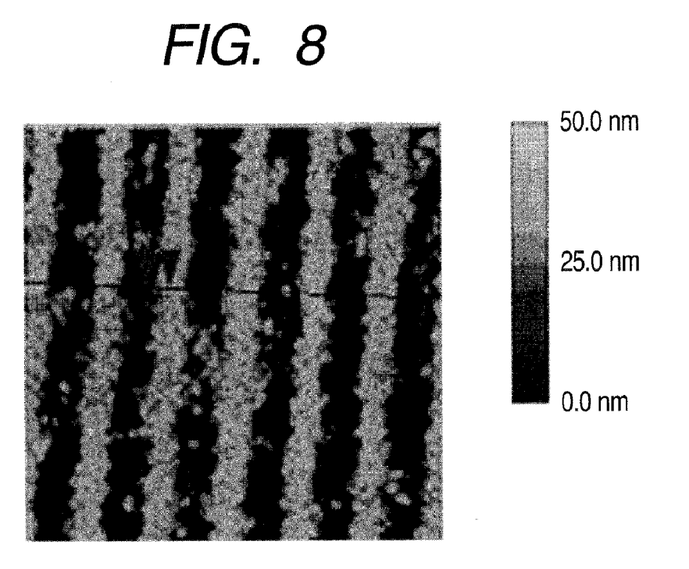
FIG. 8 is an atomic force photomicrograph of 1 μm² of a resist pattern having a film thickness of 10 nm and a pitch of 160 nm employing photosensitive composition M.
Figure 9:
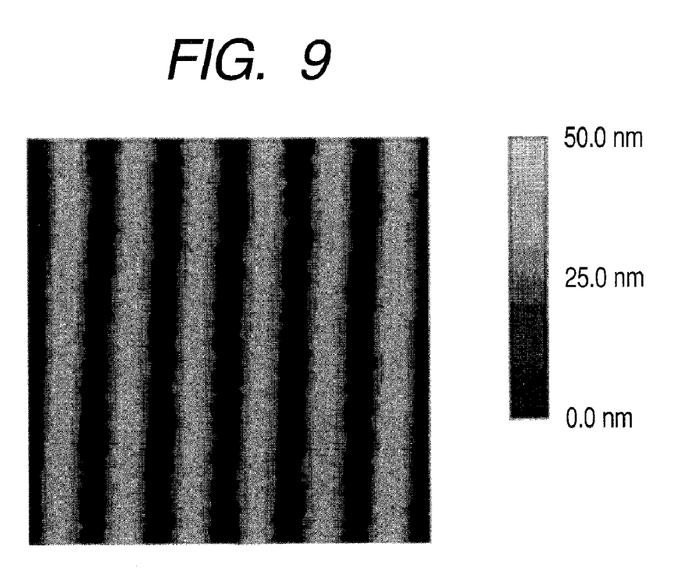
FIG. 9 is an atomic force photomicrograph of 1 μm² of a resist pattern having a film thickness of 20 nm and a pitch of 160 nm employing photosensitive composition A.
Figure 10:
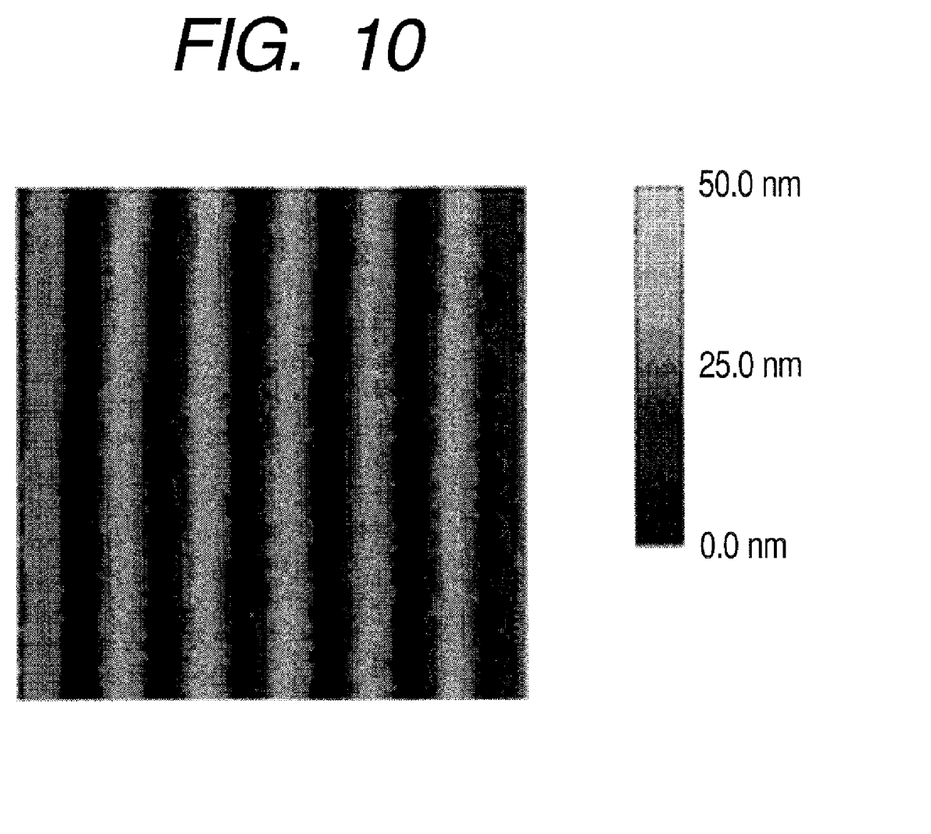
FIG. 10 is an atomic force photomicrograph of 1 μm² of a resist pattern having a film thickness of 10 nm and a pitch of 160 nm employing photosensitive composition A.

Several resist patterns were formed by changing the quantity of the projected light. FIGS. 5A and 5B are atomic force photomicrographs (AFM) of the resist patterns of the highest resolution on the respective substrates. FIG. 5A is an atomic force photomicrograph of a resist pattern of a 90 nm pitch of Photosensitive Composition M. FIG. 5B is an atomic force photomicrograph of a resist pattern of a 90 nm pitch of Photosensitive Composition A".

As shown above, Photosensitive Composition A" enables formation of a resist pattern with sufficiently small LER in comparison with Photosensitive Composition M.

Example 6

Formation of Resist Pattern by Near-Field Light Exposure (2)

Two resist-coated substrates coated with Photosensitive Composition A" in a film thickness of 20 nm or 10 nm, and three resist-coated substrates coated with Photosensitive Composition M in a film thickness of 30 nm, 20 nm, or 10 nm were prepared in the same manner as in Example 5.

A photomask was employed which was the same as the one of Example 5 except that the pattern on the amorphous light absorber had a pitch of 160 nm, and a space breadth of about 60 nm. The resist-coated substrates with the photomask closely attached were subjected to near-field light exposition.

After the light exposure, the resist-coated substrates were subjected to heating and development to form resist patterns of a 160 nm pitch.

On the respective resist-coated substrates, resist patterns were formed by changing the quantity of the light. FIGS. 6 to 10 are atomic force photomicrographs of the resist patterns having the highest resolution of the respective patterns.

As shown in the atomic force photomicrographs, Photosensitive Compound M tended to give a larger LER at a smaller film thickness range from 30 to 10 nm. Photosensitive Compound A" gave a resist pattern of a small LER even with the film thickness of 10 nm.

Photosensitive Composition M gave a large LER at a film thickness of 10 nm probably because the dilution with PGMEA of Photosensitive Composition M composed of multiple components for a smaller film thickness caused deviation of the composition ratio in application onto the substrate.

Further, the chemically amplified resist is generally known to cause abnormality of the pattern owing to neutralization of the acid generated at the exposed portion, on the surface, by a basic component existing in the environmental atmosphere. This effect could become remarkable in the film thickness of 10 nm or less.

As described above, the present invention provides a process for forming a resist pattern by employing a photosensitive composition capable of forming a resist pattern with a small LER, and provides also a process for producing a device employing the resist pattern.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-161524, filed on Jun. 9, 2006 and 2007-027368, filed on Feb. 6, 2007, which are hereby incorporated by reference herein in their entirety.

The invention claimed is:

1. A process for forming a resist pattern comprising the steps of:

applying a photosensitive composition comprising at least one compound dissolved in an organic solvent selected from the group consisting of a photosensitive compound having, in the molecule, two or more structural units represented by General Formula (1):

where $R_1$ is a hydrogen atom or an alkyl group; at least one of $R_2$, $R_3$, $R_4$, $R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom; and $R_7$ is a substituted or unsubstituted phenylene or naphthylene group, and a photosensitive compound having, in the molecule, two or more structural units represented by General Formula (6):

(6)

where $R_1$ is a hydrogen atom or an alkyl group; at least one of $R_2$, $R_3$, $R_4$, $R_5$, and $R_6$ is a nitro group, and others are selected from the group consisting of a hydrogen atom, a halogen atom, an alkyl, an alkoxy, a phenyl, a naphthyl, and an alkyl in which a part or the entire of hydrogen atoms are substituted by a fluorine atom; and $R_7$ is a substituted or unsubstituted phenylene or naphthylene group, on a substrate to form a photosensitive resist layer, irradiating the resist layer selectively with a radiation ray, and developing a portion irradiated by the ray to form a pattern of the resist layer.

2. The process for forming a resist pattern according to claim 1, wherein a resist layer capable of being removed by plasma etching and another resist layer resistant to plasma etching are laminated, and the photosensitive resist layer is formed on the layer resistant to plasma etching.

3. The process for forming a resist pattern according to claim 1, wherein the photosensitive resist layer is formed in a thickness not more than 20 nm.

4. The process for forming a resist pattern according to claim 1, wherein the irradiation of the radiation ray is conducted with near-field light.

5. A process for producing a device, in which the device is formed on a substrate by the process for forming a resist pattern set forth in claim 1.

* * * * *